United States Patent [19]

Adachi et al.

[11] 4,195,999
[45] Apr. 1, 1980

[54] SILVER HALIDE PHOTOGRAPHIC MATERIAL CONTAINING ULTRAVIOLET LIGHT ABSORBING AGENT

[75] Inventors: Keiichi Adachi; Shigeo Hirano; Tadashi Ikeda; Takeshi Mikami, all of Minami-ashigara, Japan

[73] Assignee: Fuji Photo Film Co., Ltd., Minami-ashigara, Japan

[21] Appl. No.: 896,870

[22] Filed: Apr. 17, 1978

[30] Foreign Application Priority Data

Apr. 15, 1977 [JP] Japan ............................. 52-43278

[51] Int. Cl.² .................. G03C 1/84; G03C 1/76; G03C 1/72; G03C 1/06
[52] U.S. Cl. ........................ 430/507; 252/300; 430/512; 430/527; 430/566
[58] Field of Search ................. 96/84 UV, 74, 84 R, 96/95, 112, 114, 69; 252/300

[56] References Cited

U.S. PATENT DOCUMENTS

| | | | |
|---|---|---|---|
| 2,322,005 | 6/1943 | Fierke et al. | 96/97 |
| 3,278,448 | 10/1966 | Laurer et al. | 96/84 UV |
| 4,045,229 | 8/1977 | Weber et al. | 96/84 UV |

FOREIGN PATENT DOCUMENTS

1963995  7/1971  Fed. Rep. of Germany ....... 96/84 UV

*Primary Examiner*—Richard L. Schilling
*Attorney, Agent, or Firm*—Sughrue, Rothwell, Mion, Zinn and Macpeak

[57] ABSTRACT

A silver halide photographic material comprising a support having thereon at least one silver halide photographic emulsion layer with the silver halide photographic material containing, as an ultraviolet light absorbing agent, at least one compound having the general formula (I)

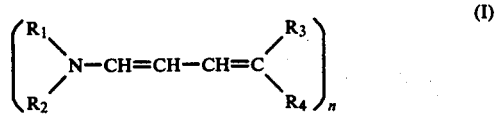

wherein $R_1$ and $R_2$, which may be the same or different, each represents a hydrogen atom, an alkyl group having 1 to 20 carbon atoms, or an aryl group having 6 to 20 carbon atoms, provided that the both of $R_1$ and $R_2$ do not simultaneously represent hydrogen atoms, and further, $R_1$ and $R_2$ can combine and form a cyclic amino group; $R_3$ represents a carboxyl group, —$COOR_5$, —$COR_5$ or —$SO_2R_5$, and $R_4$ represents a carboxyl group, —$COOR_6$, or —$COR_6$ wherein $R_5$ and $R_6$, which may be the same or different, each represents an alkyl group having 1 to 20 carbon atoms, or an aryl group having 6 to 20 carbon atoms and further, $R_5$ and $R_6$ can combine together and form a 1,3-dioxocyclohexane nucleus, a barbituric acid nucleus, a 1,2-diaza-3,5-dioxocyclopentane nucleus, or a 2,4-diazo-1-alkoxy-3,5-dioxocyclohexene nucleus; n is an integer of 1 or 2 and when n is 2, at least one of $R_1$, $R_2$ and $R_6$ may represent an alkylene or arylene group whereby the compound is a dimer; and a method of preventing the effects of ultraviolet light on a silver halide photographic material comprising incorporating into the silver halide photographic material, as an ultraviolet light absorbing agent, at least one compound having the general formula (I) above.

25 Claims, No Drawings

SILVER HALIDE PHOTOGRAPHIC MATERIAL CONTAINING ULTRAVIOLET LIGHT ABSORBING AGENT

BACKGROUND OF THE INVENTION

1. Field of the Invention

This invention relates to silver halide photographic materials, and more particularly to those in which an ultraviolet light absorbing agent is incorporated into the photographic materials to reduce the harmful effects of ultraviolet light. The present invention also relates to a method of eliminating the harmful effects of ultraviolet light on silver halide photographic materials.

2. Description of the Prior Art

It is quite well known that ultraviolet light is harmful to photographic materials in many respects. Generally speaking, a photographic material, comprising a support of relatively high electric insulation such as films of cellulose triacetate, poly(ethylene terephthalate), polystyrene or polycarbonate, and paper laminates covered by such films and a light sensitive, photographic emulsion coating mainly comprising silver halide provided on the support, has surfaces of a fairly high electric insulative nature. Hence, during the manufacture and handling of the photographic material, the surfaces tend to be electrostatically charged through contact and friction with or separation from a foreign material of the same or different compositions. When the generated electrical charge accumulates to a certain critical level, the electrical charge discharges into the air forming discharging sparks. A photographic material, which has been subjected to such discharging sparks, has various irregular discharge patterns, such as arborescent, feather-like, spotty or radial patterns, thereon after development. These undesirable patterns occurring due to the above-described reason are referred to, in general, as static marks in the photographic art.

It is also well known in the photographic art that the spark light responsible for static marks is spectrally distributed between wavelengths of about 200 and about 550 nm, and that light between wavelengths of about 300 and 400 nm is most abundant energetically. Therefore, as described in, for example, Japanese Patent Publication No. 10726/1975, Japanese Patent Application (OPI) No. 26,021 (the term "OPI" as used herein refers to a "published unexamined Japanese patent application"), French Pat. No. 2,036,679, etc., various attempts have been made to reduce the generating frequency of static marks by using a UV absorbing agent which effectively absorbs light between about 300 and about 400 nm to prevent the UV light from reaching the photo-sensitive layer.

Separately, except for lith-films and X-ray films which are used with specific light sources, general purpose photographic materials are also adversely affected by UV light present in the light used for image exposure. For example, monochromatic photographic materials tend to produce disadvantageously low contrast images when exposed to objects reflecting a large amount of UV light such as snow-covered landscapes, seashores or the sky. Color photographic materials, which are expected to record visible light only, suffer from the effects of UV light. As an example, objects such as distant landscapes, snow scenes, asphalt-paved roads, etc. which are abundant with UV region light tend to assume a cyan appearance. In addition, the color reproduction characteristics of photographic pictures obtained by the use of various light sources (sunlight, incandescent lamps and fluorescent lamps) depend to a great extent on the kind of light source used. One reason of this dependence is the difference in the spectral energy in the UV region present in the light. An exposure with an incandescent lamp causes the color image to be more reddish than that with sunlight, while an exposure with a fluorescent lamp will cause the color image to have a more bluish tint than that with sunlight. Accordingly, in order to achieve a correct color reproduction, prevention of UV light from reaching the silver halide photo-sensitive layers in the photographic film is quite effective. Various descriptions of this approach appear in, for example, Japanese Patent Publication No. 49029/1977 and U.S. Pat. No. 4,045,229, etc.

Moreover, color pictures, particularly those comprising dyes resulting from color development, are susceptible to UV light, which causes the dye image to fade and a discoloration thereof. On the other hand, the dye precursers remaining in the emulsion coating after color development produce a color stain when subjected to the action of UV light. Such a color stain is self-evidently undesirable for the finished product print. Of the variety of color photographic products available, reflection-type, positive prints are most likely to be subjected to UV radiation, since they are frequently observed under an intense illumination of sunlight which contains a large amount of UV light. The fading and discoloration of dye images are particularly promoted by light with wavelengths between about 300 and about 400 nm. In order to reduce the effect of the UV light in this wavelength region, various UV absorbing agents have been developed including those described in, for example, U.S. Pat. Nos. 3,215,530, 3,707,375, 3,705,805, 3,352,681, 3,278,448, 3,253,921, 3,738,837 and 4,045,229, Japanese Patent Publication Nos. 26,138/1974 and 25,337/1975, and British Pat. No. 1,338,265. U.S. patent application Ser. No. 896,871 filed simultaneously herewith discloses photographic materials containing novel UV absorbing agents.

UV absorbing agents for photographic products used to eliminate the various harmful effects of UV light described above should preferably have the following characteristics:

(1) Complete or substantial transparency to visible light
(2) Good compatibility with the binder material
(3) Inertness to the photographic additives present in the silver halide light-sensitive member as well as in the photographic processing solutions
(4) High efficiency of UV light absorption, particularly in the wavelength region between about 300 and about 400 nm.
(5) High stability to the action of UV light, heat and humidity.

Most conventional UV absorbing agents employed in silver halide photographic materials not only do not meet these requirements, but also were not suited for the present purposes. For example, benzotriazole derivatives set forth in U.S. Pat. No. 3,253,921 and cinnamic acid derivatives set forth in U.S. Pat. Nos. 3,707,375 and 3,705,805, both of which have been extensively employed in photographic materials, have poor absorption characteristics in the spectral region between about 300 and about 400 nm, particularly between 365 and 400 nm with a broad tail near 400 nm.

Accordingly, such a UV absorber needs to be incorporated in a relatively high concentration in order to ensure the necessary absorbance, in which case, however, a considerable fraction of blue light with wavelengths longer than 415 nm is also absorbed, resulting in a decrease in the photographic speed and an undesirable coloration (stain). Therefore, the amount in the photographic material must be suppressed, and thus effective absorption of the UV light of wavelengths between about 365 and about 400 nm is not achieved, and satisfactory improvements in static mark prevention, color reproduction characteristics and light fastness of the dye images are not obtained. Incorporation of a UV absorber in an amount sufficiently high to effectively achieve such improvement often results in additional technical problems including, for example, a poor adhesion between different coatings superimposed to form a multi-layer photographic material, and a deterioration in the physical properties of the film as represented by an increased tendency toward surface blocking, etc.

SUMMARY OF THE INVENTION

An object of the present invention is to provide a method of preventing static marks, and fading and discoloration of dye images, all caused by UV radiation, and to provide a silver halide photographic material in which the harmful effects of UV light are effectively eliminated.

Another object of the present invention is to provide a silver halide photographic material containing a UV absorbing agent which efficiently eliminates the actions of UV light without adversely affecting the various photographic characteristics such as photographic speed and fog density and also the physical properties of the resulting coating such as adhesion.

The above-described and other objects have been achieved in one embodiment of this invention by a silver halide photographic material comprising a support having thereon at least one silver halide photographic emulsion layer with the silver halide photographic material containing, as an ultraviolet light absorbing agent, at least one compound represented by the following general formula (I)

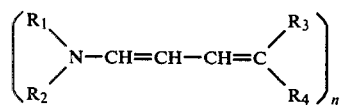  (I)

wherein $R_1$ and $R_2$, which may be the same or different, each represents a hydrogen atom, an alkyl group having 1 to 20 carbon atoms or an aryl group having 6 to 20 carbon atoms, with the proviso that both of $R_1$ and $R_2$ do not simultaneously represent a hydrogen atom, and $R_1$ and $R_2$ can combine and represent the atoms necessary to complete a cyclic amino group; $R_3$ represents a carboxy group, $-COOR_5$, $-COR_5$ or $-SO_2R_5$; $R_4$ represents a carboxy group, $-COOR_6$ or $-COR_6$, wherein $R_5$ and $R_6$, which may be the same or different, each represents an alkyl group having 1 to 20 carbon atoms or an aryl group having 6 to 20 carbon atoms or $R_5$ and $R_6$ can combine to form a 1,3-dioxocyclohexane nucleus, a barbituric acid nucleus, a 1,2-diazo-3,5-dioxocyclopentane nucleus or a 2,4-diaza-1-alkoxy-3,5-dioxocyclohexene nucleus; and n represents an integer of 1 or 2, and when n is 2, at least one of $R_1$, $R_2$ and $R_6$ represents an alkylene group or an arylene group and the compound of the general formula (I) is a dimer.

The above-described and other objects have also been achieved in another embodiment of this invention by a method of preventing the effects of ultraviolet light on a silver halide photographic material comprising a support having thereon at least one silver halide photographic emulsion layer by incorporating into said silver halide photographic material, as an ultraviolet light absorbing agent, at least one compound represented by the general formula (I) described above.

DETAILED DESCRIPTION OF THE INVENTION

In the above general formula (I), $R_1$ and $R_2$ each represents a hydrogen atom but both $R_1$ and $R_2$ cannot simultaneously be a hydrogen atom. $R_1$ and $R_2$ also can represent an alkyl group (which preferably has from 1 to 20 carbon atoms, may be straight chain, branched or cyclic, and may be substituted with one or more of a hydroxy group, a halogen atom (e.g., a chlorine atom, a bromine atom, a fluorine atom, etc.), an aryl group (e.g., a phenyl group, a naphthyl group, a tolyl group, etc.), an alkoxycarbonyl group (e.g., a methoxycarbonyl group, an ethoxycarbonyl group, a dodecyloxycarbonyl group, a tetradecyloxycarbonyl group, etc.), an alkoxy group (e.g., a methoxy group, an ethoxy group, a propoxy group, a methoxyethoxy group, a hydroxyethoxy group, etc.), an alkylcarbonyl group (e.g., an acetyl group, a valeryl group, etc.), an arylcarbonyl group (e.g., a benzoyl group, a toluoyl group, a naphthoyl group, etc.), an alkylcarbonyloxy group (e.g., an acetoxy group, a valeryloxy group, a stearoyloxy, etc.), an arylcarbonyloxy group (e.g., a benzoyloxy group, a toluoyloxy group, etc.), a cyano group, an alkylsulfonyl group (e.g., a mesyl group, an ethanesulfonyl group, etc.), an arylsulfonyl group (e.g., a tosyl group, a benzenesulfonyl group, etc.), a carbamoyl group, an N,N-dialkylcarbamoyl group (e.g., an N,N-diethylcarbamoyl group, an N,N-dibutylcarbamoyl group, etc.), an N-alkyl-N-arylcarbamoyl group (e.g., an N-ethyl-N-phenylcarbamoyl group, an N-methyl-N-tolylcarbamoyl group, etc.), an N-alkylcarbamoyl group (e.g., an N-(n-butyl)carbamoyl group, an N-ethylcarbamoyl group, etc.), a morpholinocarbonyl group, a sulfo group, a carboxy group, an N,N-dialkylamino group (e.g., an N,N-dimethylamino group, an N,N-diethylamino group, etc.), an aryloxy group (e.g., a phenoxy group, a tolyloxy group, etc.), and a furyl group, etc. and may contain an unsaturated linkage in the carbon chain. Examples of suitable alkyl groups for $R_1$ and $R_2$ include methyl, ethyl, butyl, n-hexyl, cyclohexyl, n-decyl, n-dodecyl, n-octadecyl, eicosyl, methoxyethyl, ethoxypropyl, 2-ethylhexyl, hydroxyethyl, chloropropyl, N,N-diethylaminopropyl, cyanoethyl, phenethyl, benzyl, p-t-butylphenethyl, p-t-octylphenoxyethyl, 3-(2,4-di-tert-amylphenoxy)propyl, ethoxycarbonylmethyl, 2-(2-hydroxyethoxy)ethyl, 2-furylethyl, etc.). $R_1$ and $R_2$ further can represent an aryl group (preferably having 6 to 20 carbon atoms and which may be monocyclic or bicyclic and may be substituted with one or more of a hydroxy group, a halogen atom (e.g., a chlorine atom, a bromine atom, a fluorine atom, etc.), a cyano group, an alkoxy group (e.g., a methoxy group, an ethoxy group, a propoxy group, a methoxyethoxy group, etc.), an alkyl group (e.g., a methyl group, an ethyl group, a tert-amyl group, etc.), etc. Examples of suitable groups are tolyl, phenyl, anisyl, mesityl, chlorophenyl, 2,4-di-tert-amylphenyl, naphthyl, etc. Also, $R_1$ and $R_2$ can combine and form a monocyclic or bicyclic heterocyclic amino group, preferably a 5- to 7-membered ring, and which may contain one or more nitrogen atoms, oxygen atoms or sulfur atoms in addition to the nitrogen atom to which the $R_1$ and $R_2$ moieties are attached. Suitable examples of heterocyclic amino groups include a 2-pyrroline ring, a 3-pyrroline ring, a pyrrolidine ring, an indoline ring, a piperidine ring, a piperazine ring, a pyrazole ring, an imidazole ring, a 2-imidazoline ring, an imidazolidine ring, a benzimidazole ring, an imidazine ring, a triazole ring, a benzotriazole ring, a purine ring, an oxazine ring, a morpholine ring, a thiazine ring, an azepine ring, a hexahydroazepine ring, etc. The above described heterocyclic amino groups may also be substituted with one or more of an alkyl group (e.g., a methyl group, an ethyl group, a tert-amyl group, etc.), a hydroxy group, a halogen atom (e.g., a chlorine atom, a bromine atom, a fluorine atom, etc.), a cyano group, an alkoxy group (e.g., a methoxy group, an ethoxy group, a propoxy group, etc.), an aryl group (e.g., a phenyl group, a naphthyl group, etc.), etc.

As described above $R_3$ represents a carboxy group, —$COR_5$, —$COOR_5$ or —$SO_2R_5$, and $R_4$ represents a carboxy group, —$COR_6$ or —$COOR_6$ and $R_5$ and $R_6$ each represents an alkyl group or an aryl group, each having the same meanings as those for $R_1$ and $R_2$. Further, $R_5$ and $R_6$ may combine together and represent the atomic groups necessary to complete a 1,3-dioxocyclohexane ring (e.g., dimedone, 1,3-dioxo-5,5-diethylcyclohexane, etc.), a 1,3-diazo-2,4,6-trioxocyclohexane ring (e.g., barbituric acid, 1,3-dimethylbarbituric acid, 1-phenylbarbituric acid, 1-methyl-3-octylbarbituric acid, etc.), a 1,2-diaza-3,5-dioxocyclopentane ring (e.g., 1,2-diaza-1,2-dimethyl-3,5-dioxocyclopentane, 1,2-diaza-1,2-diphenyl-3,5-dioxocyclopentane, etc.), or a 2,4-diazo-1-alkoxy-3,5-dioxocyclohexane ring (e.g., 2,4-diazo-1-ethoxy-4-ethyl-3,5-dioxocyclohexene, 2,4-diazo-1-ethoxy-4-[3-2,4-di-tert-amylphenoxy)propyl]-3,5-dioxocyclohexene, etc.).

n in the above general formula (I) represents 1 or 2 and when n is equal to 2, at least one of $R_1$, $R_2$ and $R_6$ may represent an alkylene or arylene group whereby the compound is a dimer.

Of the UV absorbing compounds represented by general formula (I), particularly preferred compounds are those which are liquid at room temperature (about 25° C.) or which are solid with a melting point of about 130° C. or less.

Of the compounds of the general formula (I), those represented by the following general formula (II) are particularly preferred:

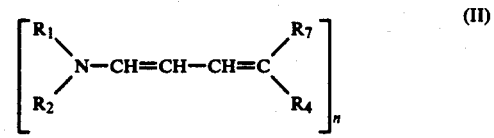

wherein $R_1$, $R_2$, $R_4$ and n have the same meaning as in the general formula (I) and $R_7$ represents —$COOR_6$ or —$SO_2R_6$ wherein $R_6$ has the same meaning as in the general formula (I).

Typical examples of compounds represented by general formula (I) are shown below by structural formulae together with their absorption maxima measured at $1 \times 10^{-5}$ mole/(liter methanol) concentration at room temperature (about 25° C.).

| | MeOH $\lambda_{max}$ |
|---|---|
| Compound 1 $(n)\text{-}C_6H_{13}\diagdown\atop(n)\text{-}C_6H_{13}\diagup N\text{--}CH=CH\text{--}CH=C\diagup^{CO_2C_2H_5}_{\diagdown SO_2\text{--}C_6H_5}$ | 373 nm |
| Compound 2 $(n)\text{-}C_4H_9\diagdown\atop(n)\text{-}C_4H_9\diagup N\text{--}CH=CH\text{--}CH=C$ (dimedone ring, $CH_3$, $CH_3$) | 389 nm |
| Compound 3 $CH_3\diagdown\atop CH_3\diagup N\text{--}CH=CH\text{--}CH=C\diagup^{CO_2CH_2\text{--}CH(C_2H_5)\text{--}C_4H_9\text{-}(n)}_{\diagdown CO_2CH_2\text{--}CH(C_2H_5)\text{--}C_4H_9\text{-}(n)}$ | 374 nm |
| Compound 4 $(n)\text{-}C_6H_{13}\diagdown\atop(n)\text{-}C_6H_{13}\diagup N\text{--}CH=CH\text{--}CH=C\diagup^{COCH_3}_{\diagdown COCH_3}$ | 395 nm |
| Compound 5 | |

-continued
| | MeOH $\lambda_{max}$ |
|---|---|
|   Compound 7 | 395 nm |
|   Compound 8 | 388 nm |
|   Compound 9 | 374 nm |
|   Compound 10 | 385 nm |
|   Compound 11 | 373 nm |
|   Compound 12 | 383 nm |
|   Compound 13 | 389 nm |
|  | 385 nm |

|  | MeOH $\lambda_{max}$ |
|---|---|
| <br>Compound 14 | 394 nm |
| 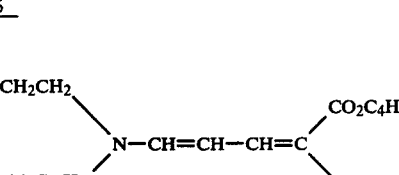<br>Compound 15 | 375 nm |
| 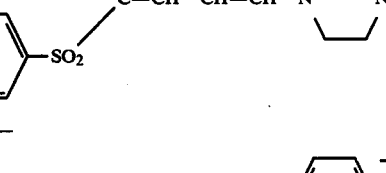<br>Compound 16 | 387 nm |
| 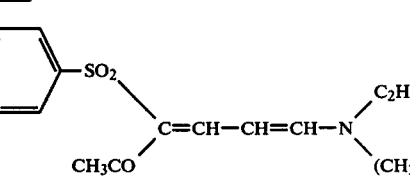<br>Compound 17 | 375 nm |
| 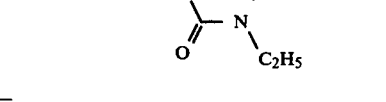<br>Compound 18 | 383 nm |
| 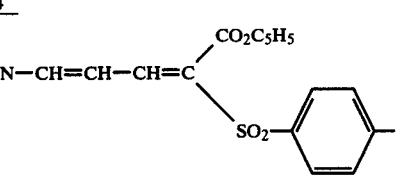<br>Compound 19 | 374 nm |
| 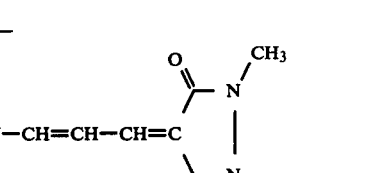<br>Compound 20 | 385 nm |
| 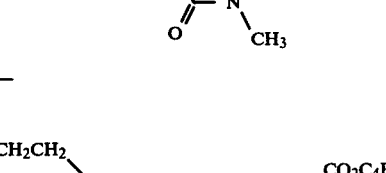<br>Compound 21 | 389 nm |

|  | MeOH $\lambda_{max}$ |
|---|---|
| 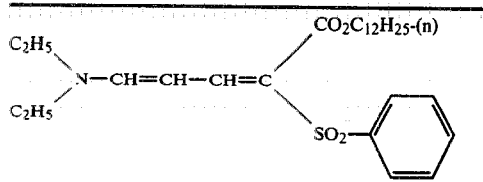 | 372 nm |
| Compound 22 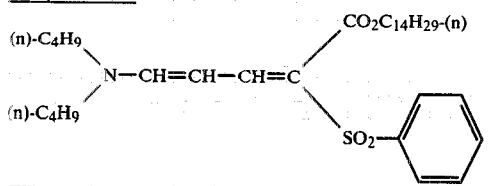 | 372 nm |

The ultraviolet light absorbing agent having the general formula (I) used in this invention can be prepared according to the method described in U.S. Pat. No. 4,045,229, etc.

Specific procedures for synthesizing representative examples of compounds of the present invention are described below. Unless otherwise indicated, all parts, percents, ratios and the like are by weight.

SYNTHESIS EXAMPLE 1

Synthesis of Compound 1

13.3 g of 3-anilinoacroleinanil and 14.3 g of ethylphenylsulfonyl acetate were heated at 85°–90° C. for 2 hours in 40 ml of acetic anhydride. After the removal of the acetic anhydride under reduced pressure, 40 ml of ethanol and 24.1 g of di-n-hexylamine were added to the mixture, which was then refluxed for 2 hours. Then, the ethanol was removed by distillation, and the residue was passed through a chromatographic column charged with "Kieselgel 60" (a product of Merck Co.) and the benzene efluent was collected, from which 18 g of Compound 1 was separated by recrystallization from ethanol. The product had a melting point of 95°–96° C.

SYNTHESIS EXAMPLE 2

Synthesis of Compound 4

13.0 g of 3-anilinoacroleinanil was mixed with 40 ml of acetic anhydride with exothermic heat of reaction being generated. After heating at 80° C. for 10 minutes, the acetic anhydride was removed under a reduced pressure. Then 20 g of di-n-hexylamine was added to the reaction vessel to cause a vigorous reaction. The reaction was allowed to proceed for 20 minutes. After the removal of the excess amine under reduced pressure, 4.5 g of acetylacetone was added. The reaction system was heated at 80° C. for 30 minutes. Finally, Compound 4 was obtained by distillation at 180°–190° C. and 0.02 mm Hg. The yield was 12 g.

The compounds characterizing the present invention are essentially insoluble in water and some of them are oily liquids at room temperature.

The UV absorbing compounds represented by general formula (I) used in the present invention have far higher extinction for light of wavelengths between about 360 and aboug 395 nm as compared with other, well-known UV absorbing agents conventionally used in silver halide photographic materials (such as benzotriazole derivatives disclosed in, for example, U.S. Pat. No. 3,253,921, or cinnamic acid derivatives set forth in U.S. Pat. No. 3,705,805). This enables the necessary optical density to be achieved at a relatively low amount in the photographic material. It should be noted that in the spectral region over about 410 nm the compounds of the general formula (I) exhibit substantially no light absorption. Accordingly, a photographic print containing such a UV absorbing agent does not have any undesirable color.

The compounds used in the present invention can be added to a silver halide photographic material using any of the following dispersion techniques.

Firstly, the UV absorbing compound is dissolved in a substantially water-insoluble, high-boiling point organic solvent (e.g., an alkyl ester of phthalic acid including dibutyl phthalate, dioctyl phthalate, etc., a trimellitic acid ester such as tri-t-octyl trimellitate, an aromatic ether such as anisole, phenetole, phenyl ether, etc., a phosphoric acid ester such as diphenyl phosphate, triphenyl phosphate, tricresyl phosphate, dioctylbutyl phosphate, etc., a citric acid ester such as tributyl acetylcitrate, an alkyl amide such as N,N-diethyllaurylamide), and the resulting solution is emulsified into an aqueous hydrophilic organic colloid solution, for example, as disclosed in U.S. Pat. No. 2,322,027.

Secondly, the UV absorbing agent can be emulsified in a similar manner to the first method using an auxiliary solvent (e.g., a water-miscible solvent such as methanol, acetone, methyl Cellosolve, etc., or a substantially water-immiscible solvent such as ethyl acetate, butyl acetate, etc., as disclosed for example, in U.S. Pat. Nos. 2,739,888 and 3,351,681, Japanese Patent Publication No. 59943/1976, etc.

Thirdly, the compound of the present invention can be dissolved in an organic solvent (including water-inmiscible, high-boiling point organic solvents, substantially water-immiscible, low-boiling point organic solvents, water-miscible organic solvents, etc.) (where the compound itself is an oil, the use of solvent may be omitted.), and the resultant solution is incorporated into an aqueous polymer latex or into a polymer latex containing a hydrophilic colloid whereby the UV absorbing agent used in the present invention is absorbed in the individual latex particles. This method is disclosed, for example, in Japanese Patent Publication No. 39853/1976, Japanese Patent Application (OPI) Nos. 59942/1976 and 59943/1976.

Fourthly, the compound can be directly dispersed into a hydrophilic organic colloid coating mixture containing photosensitive silver halide grains, after being dissolved in a water-miscible solvent such as acetone, methyl Cellosolve, methanol, ethanol, etc.

Fifthly, where the compound itself is oily at room temperature, the compound can be dispersed directly in a hydrophilic organic colloid solution, and the resultant dispersion is added to the photographic coating mixture.

Of these procedures, the first three methods are particularly advantageous for the purposes of the present invention.

The UV absorbing agent used in the present invention can be emulsified using about 0.1 to 10 ml, preferably, 0.2 to 4 ml, of an organic solvent having a low volatility per gram of the UV absorbing agent. When a polymer latex is used for dispersion, the weight of such a polymer latex amounts to from about 0.1 to about 10 g, and more preferably from 0.2 to 6 g per gram of the UV absorbing agent.

A suitable coating rate of the UV absorbing agent used in the present invention ranges from about 5 to about 1500 mg per m$^2$ of the silver halide photographic material. Preferred ranges for different types of photographic materials are about 50 to about 1500 mg/m$^2$ for a color print material (e.g., a color paper and a positive color film), and about 5 to about 650 mg/m$^2$ for a color material for camera use (e.g., a negative color film and a color reversal film).

The reduced content of the UV absorbing agent used in the present invention, mainly due to a higher functional efficiency, makes the resulting photographic material free of deterioration in adhesion between continuous coatings forming a multi-layer structure and also of tendency toward surface blocking. Moreover, emulsified dispersions and solutions of water-miscible organic solvents containing the compounds used in the present invention are stable without showing any tendency toward particle coagulation or crystal separation. When the compounds used in the present invention are incorporated either in a light-sensitive silver halide photographic emulsion coating or in a light-insensitive hydrophilic colloid layer (e.g., a gelatin coating), the layer does not become opaque. The compounds used in the present invention are quite stable against heat when they are present in silver halide light-sensitive elements.

The compounds used in the present invention can be employed together with various photographic additives such as conventionally known UV absorbing agents including those set forth in U.S. Pat. Nos. 3,253,921, 3,707,375, 3,705,805, 3,271,156, 3,754,919, 3,794,493, 3,692,525, 3,738,837, 3,698,907, 3,936,305, 3,687,671 and 3,694,211, British Pat. No. 1,338,265, Japanese Patent Publication Nos. 25337/1975, 26138/1974, etc., conventionally known anti-oxidants (e.g., hydroquinone derivatives, catechol derivatives, aminophenol derivatives, gallic acid derivatives, etc.) and color image formers such as color couplers well known in the art.

Gelatin is advantageously used as the hydrophilic colloid in these layers but other hydrophilic colloids may be used. For example, gelatin derivatives; graft polymers of gelatin and other polymers; proteins such as albumin, casein, etc.; cellulose derivatives such as hydroxyethyl cellulose, carboxymethyl cellulose, cellulose sulfuric acid esters, etc.; saccharide derivatives such as sodium alginate, starch derivatives, etc.; and various synthetic hydrophilic polymers such as polyvinyl alcohol, polyvinyl alcohol partial acetal, poly-N-vinyl-pyrrolidone, polyacrylic acid, polymethacrylic acid, polyacrylamide, polyvinylimidazole, polyvinylpyrazole etc.; can be used in this invention.

Specific examples of gelatin derivatives which can be used as the hydrophilic colloid in this invention are those obtained by reacting gelatin and various compounds such as acid halides, acid anhydrides, isocyanates, bromoacetic acid, alkanesultones, vinylsulfonamides, maleinimide compounds, polyalkylene oxides, epoxy compounds, etc. These materials are described in, for example, U.S. Pat. Nos. 2,614,928, 3,132,945, 3,186,846, 3,312,553, British Pat. Nos. 861,414, 1,033,189 and 1,005,784 and Japanese Patent Publication No. 26845/1967.

Examples of the above-described graft polymers of gelatin include graft polymers formed by grafting gelatin to homopolymers or copolymers of vinylic monomers such as acrylic acid, methacrylic acid, the esters and amides of acrylic acid or methacrylic acid, acrylonitrile, styrene, etc. In particular, graft polymers of gelatin with polymers having some degree of compatibility with gelatin, such as polymers of acrylic acid, methacrylic acid, methacrylamide, acrylamide, hydroxyalkyl methacrylate, etc., are preferred. Examples of these graft polymers are described in U.S. Pat. Nos. 2,763,625, 2,831,767 and 2,965,884.

Further, typical examples of synthetic hydrophilic polymers which can be used in this invention as the hydrophilic colloid are described in, for example, German Patent Application (OLS) No. 2,312,708, U.S. Pat. Nos. 3,620,751 and 3,879,205 and Japanese Patent Publication No. 7561/1968.

The latex polymer used for the purpose described above may be selected from water-insoluble or water sparingly soluble synthetic polymers which are known as being suitable for improving the properties of films. For example, polymers composed of a monomer or monomers such as alkyl acrylates, alkyl methacrylates, alkoxyalkyl acrylates, alkoxyalkyl methacrylates, glycidyl acrylates, glycidyl methacrylates, acrylamide, methacrylamide, vinyl esters, (e.g., vinyl acetate), acrylonitrile, olefins, styrene, etc., and polymers composed of combinations of the above-illustrated monomers and acrylic acid, methacrylic acid, $\alpha,\beta$-unsaturated dicarboxylic acids, hydroxyalkyl acrylates, hydroxyalkyl methacrylates, sulfoalkyl acrylates, sulfoalkyl methacrylates, styrenesulfonic acid, etc., can be used. Examples of these synthetic polymers are described in Japanese Patent Application (OPI) No. 74538/1974, U.S. Pat. Nos. 2,376,005, 2,739,137, 2,853,457, 3,062,674, 3,411,911, 3,488,708, 3,525,620, 3,607,290, 3,625,715, 3,645,740, and British Pat. Nos. 1,186,699 and 1,307,373. Preferred examples of these polymers are, for example, alkyl acrylate copolymers (e.g., a copolymer of ethyl acrylate and acrylic acid) and the vinyl polymers described in Japanese Patent Application (OPI) No. 74538/1974.

The UV absorbing agent of the present invention can be incorporated in any one of the following hydrophilic organic colloid layers present in a silver halide photographic material, e.g., a light-sensitive silver halide emulsion coating, and various light-insensitive coatings such as, for example, a protective surface coating, a backing layer, an anti-halation layer, an intermediate layer, a subbing layer, etc.

When the photographic material is a monochromatic photographic material, the UV absorbing agent used in the present invention is preferably incorporated in a protective surface coating, a back coating or in an anti-halation coating thereof. When the photographic material is a color photographic material, the UV absorbing agent is incorporated preferably in outermost layer (e.g., a protective top coating), an intermediate layer, an anti-halation layer and a light-sensitive silver halide emulsion layer which is the farthest from the support.

The method of the present invention can be applied to photographic materials which contain at least two photographic coatings of different spectral sensitivity. Usually, a multi-layer, color photographic material contains at least one red sensitive silver halide emulsion layer, at least one green sensitive silver halide emulsion layer and at least one blue sensitive silver halide emulsion layer on a support. The order of these layers on the support can be arbitrarily chosen depending on the end use. Ordinarily, the red sensitive silver halide emulsion layer contains a cyan dye forming coupler, the green sensitive silver halide emulsion layer contains a magenta coupler and the blue sensitive silver halide emulsion layer contains a yellow coupler, respectively, although other combinations are possible for specific purposes. Further, the photographic material can contain also light-insensitive layers such as a protective layer, intermediate layers, an anti-halation layer, a back layer and a subcoating. The present invention can also be applied to multi-layered color photographic materials as disclosed in U.S. Pat. Nos. 3,726,681 and 3,516,831, British Pat. No. 923,045, German Patent Application (OLS) No. 2,018,341, etc.

Various silver halides can be used in the present invention, including silver bromide, silver chloride, silver iodobromide, silver chlorobromide, silver chloroiodobromide, etc., which can be prepared in the form of a photographic emulsion using various well-known methods. The silver halide photographic emulsion can be sensitized using a chemical sensitizer (e.g., sulfur containing sensitizers such as thiourea, allyl thiocarbamide, allyl isothiocyanate, cystine, etc. gold compounds such as potassium chloroaurate, auric trichloride, potassium auric thiocyanate, etc., and other noble metal compounds), and a reducing sensitizer well-known in the photographic art. Further, the silver halide emulsion can contain a stabilizer or an anti-foggant such as a triazole, an imidazole, an azoindene, etc.

The color photographic materials of the present invention can contain a number of color image forming agents including, for example, two or four equivalent type yellow couplers such as benzoylacetoanilide or pivaloylacetoanilide derivatives, two or four equivalent type magenta couplers such as pyrazolone or imidazolone derivatives, two or four type cyan couplers such as phenol and naphthol equivalent derivatives and colored couplers which give rise to cyan or magenta dyes. (These two equivalent type couplers described above may be of the DIR type). These couplers are desirably non-diffusing couplers. The photographic materials of this invention can also contain diffusible dye releasing redox compounds, color developing agents for couplers of the diffusible dye releasing type, etc.

Still other additives including, for example, spectral sensitizers, color stain preventing agents, anti-fading agents, hardening agents, surfactants, anti-static agents, etc., can also be incorporated into the photographic material. Examples of these compounds are described in, for example, U.S. Pat. No. 3,996,055 (column 23, line 23 to column 37, line 25); U.S. Pat. No. 3,994,729 (column 2, line 15 to column 5, line 61) and U.S. Pat. No. 3,997,348 (column 6, line 51 to column 31, line 9).

Suitable photographic products according to the present invention include black and white, high-speed photographic films, microfilms, films for the graphic arts (lith films, etc.), color negative films, color reversal films, color direct positive films, color positive papers, diffusion transfer type color materials, etc.

The photographic materials produced in accordance with the present invention can be processed in an ordinary manner or using a DTR color processing liquid incorporated in the photographic material itself. For example, the methods described in *The Journal of the Society of Motion Picture and Television Engineers*, Vol. 61 (1953), pp 667–701, can be employed.

By using a silver halide photographic material based on the present invention, not only can fog generation by static phenomena be effectively prevented during the manufacture and storage of the photographic material, but images which are quite clear can be produced due to efficient cutoff of ultraviolet light reflected by the object. Particularly in the case of a color photographic material, fluctuations in color reproduction due to the difference in UV absorption by camera lenses can be suppressed, thus providing color images of high fidelity. Further, fading or discoloration of the resulting dye images is also prevented. It is important that these advantages can be achieved without any sacrifice of properties such as photographic speed, fog, adhesive properties, and other photographic as well as physical characteristics.

In the following, some specific examples of the present invention are described below for an even better understanding of the present invention.

EXAMPLE 1

To a gelatin solution (a-1) comprising 1000 g of a 10% gelatin aqueous solution and 75 ml of a 5% aqueous solution of sodium dodecylbenzene sulfonate heated to 50° C. was added another solution (b-1) comprising 40 ml of dibutyl phthalate, 100 ml of ethyl acetate and 20 ml of a 20% methanol solution of sorbitan monolaurate kept at 50° C. The entire volume was subjected to 5 minutes of dispersion using a high-speed homogenizer. The resulting dispersion which was the control for the present example was designated Emulsified Dispersion A. Another emulsified dispersion designated Emulsified Dispersion B was prepared by adding to gelatin solution a-1 another solution b-2 which comprised Compound 1 (80 g) and the components for mixture b-1 described above.

Five additional emulsified dispersions designated Emulsified Dispersions C to G were prepared by replacing the UV absorbing agent, Compound 1, by the following compounds;

|  | Emulsified Dispersion |
|---|---|
| 80 g of Compound 8 | C |
| 20 g of 2-(2-Hydroxy-5-tert-butylphenyl)-benzotriazole, together with 80 g of Compound 1 | D |
| 120 g of 2-(2-Hydroxy-5-tert-butylphenyl)-benzotriazole | E |
| 120 g of 4-Methoxy-α-cyanocinnamic acid n-decyl ester | G |

Another gelatin solution designated a-2 was prepared by adding to gelatin solution a-1 1000 g of an aqueous polymer latex containing a copolymer comprising 95 mole% ethyl acrylate and 5 mole% acrylic acid in 10 weight % solids content. Latex Dispersion E was prepared by adding to the above prepared solution a-2 solution b-3 which was equivalent to b-2 except that dibutyl phthalate was not present.

The emulsified dispersion formulations are listed in Table 1 below.

Table 1

| Component | Emulsified or Latex Dispersion | | | | | | |
|---|---|---|---|---|---|---|---|
| | A | B | C | D | E | F | G |
| Gelatin (10% aq. soln.) | 1000g | 1000g | 1000g | 1000g | 1000g | 1000g | 1000g |
| Sodium Dodecylbenzene Sulfonate (5% aq. soln.) | 75 ml | 75 ml | 75 ml | 75 ml | 75 ml | 75 ml | 75 ml |
| Dibutyl Phthalate | 40 ml | 40 ml | 40 ml | 40 ml | — | 40 ml | 40 ml |
| Ethyl Acetate | 100 ml | 100 ml | 100 ml | 100 ml | 100 ml | 100 ml | 100 ml |
| Sorbitan Monolaurate (20% methanol soln.) | 20 ml | 20 ml | 20 ml | 20 ml | 20 ml | 20 ml | 20 ml |
| Poly(ethyl acrylate) Latex (10 wt. % solids content) | — | — | — | — | 1000 ml | — | — |
| Compound 1 | — | 80 g | — | 80 g | 80 g | — | — |
| Compound 8 | — | — | 80 g | — | — | — | — |
| 2-(2-Hydroxy-5-tert-butylphenyl)benzotriazole | — | — | — | 20 g | — | 120 g | — |
| 4-Methoxy-α-cyano-cinnamic acid n-decyl ester | — | — | — | — | — | — | 120 g |

Then, the following layers were coated on a support in the following order.

First Layer:
An antihalation layer comprising a mordant*1, gelatin and dyes*2.

Second Layer:
A red sensitive, silver iodobromide (AgI content: 4 mole %) gelatin emulsion layer with a silver/coupler mole ratio of 25:1 and a silver coating rate of 30 mg/100 cm², containing an oil soluble, non-diffusible cyan coupler*3.

Third Layer:
A gelatin interlayer

Fourth Layer:
A green sensitive, silver iodobromide (AgI content: 3.5 mole %) gelatin emulsion layer with a silver/coupler mole ratio of 35:1 and a silver coating rate of 20 mg/100 cm², containing a non-diffusible magenta coupler*4.

Fifth Layer:
A gelatin layer capable of filtering yellow light.

Sixth Layer:
A silver iodobromide (AgI content: 3 mole %) gelatin emulsion layer with a silver/coupler mole ratio of 10:1 and a silver coating rate of 15 mg/100 cm², containing a non-diffusible yellow coupler*5.

Seventh Layer:
A top coating containing a UV absorbing agent with a coating amount of 1.50 g/m², which corresponds to a coating thickness of 1.8 microns.

Seven multi-layer photographic materials were prepared, which were designated Sample (1) to Sample (7), by employing each emulsified dispersion listed in Table 1, respectively, to provide the Seventh Layer as the top coating.

The various components used in preparing the above Samples (1) to (7) were as follows:

*1 Mordant $$\text{\textendash}(CH_2\text{\textendash}CH)_x\text{\textendash}(CH_2\text{\textendash}CH)_y\text{\textendash}$$

with side groups:
C=O
|
CH₃ and
C=N—NHC(=NH)NH₂ · CH₃COOH
|
CH₃ x : y = 77 : 23 (molar ratio)

Coating amount: 0.5 g/g binder

*2 Dyes: A mixture of the following three dyes was used
Cyan Dye:

$NaO_3SH_2CNH$ ... $OH$ ... $SO_3Na$
$NaO_3S$ ... $OH$ ... $NHCH_2SO_3Na$
(anthraquinone structure)

Coating amount: about 200 mg/m²

Magenta Dye:
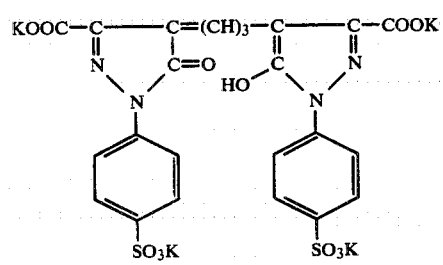
Coating amount: about 200 mg/m²
Yellow Dye:
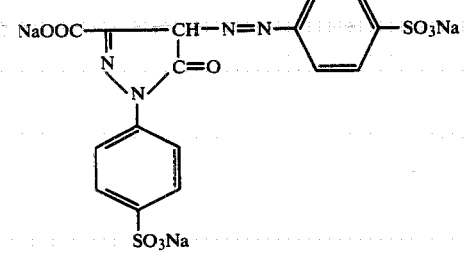
Coating amount: 200 mg/m²
*3 Cyan Coupler
(a) 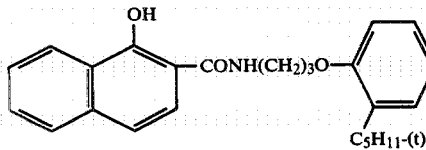 and
(b) 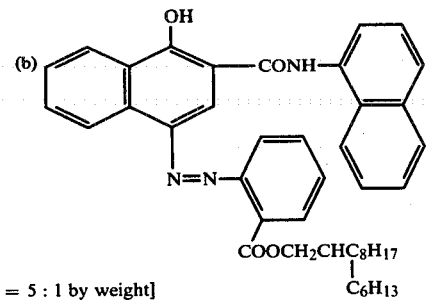
[(a) : (b) = 5 : 1 by weight]
*4 Magenta Coupler
(a) 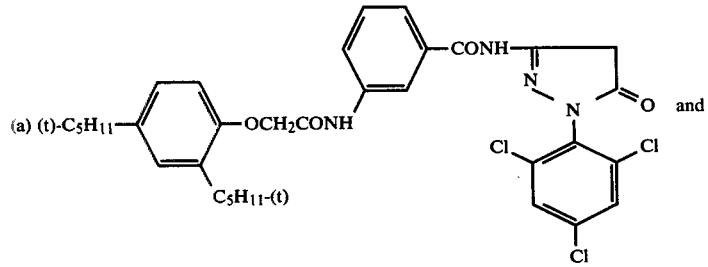 and
(b) 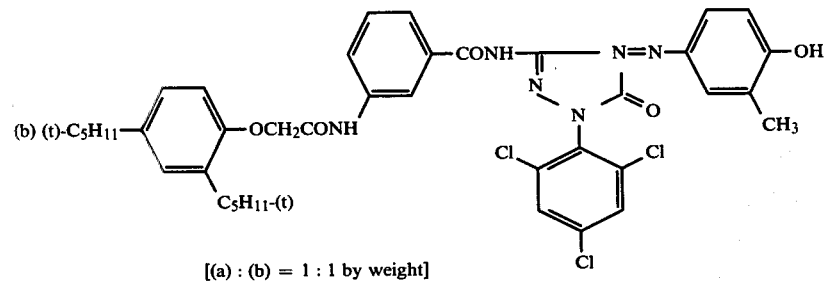
[(a) : (b) = 1 : 1 by weight]
*5 Yellow Coupler -continued

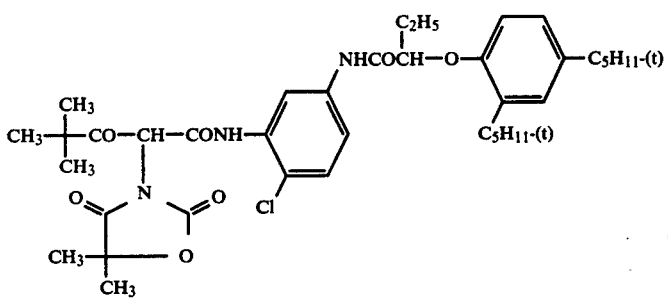

In order to evaluate the degree of color balance fluctuation due to the difference as in the transmittance of ultraviolet light of a camera lens, a standard grey chart was photographed on each of Samples (1) to (7) through a lens which transmitted UV light quite well and through the combination of the same lens and a filter which cuts light with wavelengths shorter than 390 nm. After exposure each of Examples (1) to (7) was subjected to the following processing:

Color Development: 38° C., 3 min 15 sec.
Bleach: 38° C., 6 min 30 sec.
Washing: 38° C., 3 min 15 sec.
Fixing: 38° C., 6 min 30 sec.
Stabilization: 38° C., 1 min 30 sec.

The processing solutions used in the above processing had the following compositions.

Color Developer:
Water: 800 ml
Potassium Carbonate (anhydrous): 38 g
Sodium Sulfite (anhydrous): 4 g
Sodium Bromide: 1.5 g
Hydroxylamine Sulfate: 2.5 g
EDTA: 2.5 g
4-[N-Ethyl-N-($\beta$-ethoxyethyl)amino]-2-methylaniline Sulfate: 4.7 g
Water to make: 1000 ml
pH=10.0
Bleaching Solution:
Water 600 ml
Ammonium Bromide: 150 g
EDTA-Fe(III) Sodium Salt: 100 g
Glacial Acetic Acid: 10 ml
EDTA: 10 g
Water to make: 1000 ml
pH=6.0
Fixing Solution:
Water: 800 ml
Ammonium Thiosulfate (70% aq. soln.): 140 ml
Sodium Bisulfite (anhydrous): 12 g
Water to make: 1000 ml
Stabilizing Solution:
Water: 800 ml
Formaldehyde (37% aq. soln.): 5.0 ml
Polyethylene Glycol: 0.2 g
Ethylene Glycol: 2 g
Water to make: 1000 ml The optical densities to red, green and blue lights of recorded color negative images obtained by the processing above were measured. The differences in optical density obtained with or without the filter which cut UV light are given in Table 2 below.

Table 2

| Density Fluctuation* | Sample No. | | | | | | |
|---|---|---|---|---|---|---|---|
| | (1) | (2) | (3) | (4) | (5) | (6) | (7) |
| Red | 0 | 0 | 0 | 0 | 0 | 0 | 0 |
| Green | 0 | 0 | 0 | 0 | 0 | 0 | 0 |
| Blue | 0.15 | 0.06 | 0.05 | 0.05 | 0.04 | 0.13 | 0.12 |

*The values in the above table are the density differences to red, green and blue light when images were photographed with or without a filter which cut UV light and absorbs UV light completely in the wavelength region shorter than 390 nm together with a lens which is completely transparent to UV light.

As is evident from the results in Table 2 below, Samples (2) to (5) which were prepared in accordance with the present invention, containing either Compound 1 or Compound 8, are insensitive to the change in the transmittance of UV light, exhibiting small blue light density fluctuations.

EXAMPLE 2

Another multi-layered photographic material was prepared in which the First Layer, Second Layer, Third Layer, Fourth Layer and Fifth Layer were the same as those described in Example 1. Five samples, Samples (8) to (12), were prepared by adding different emulsified dispersions as described below to the composition for the Sixth Layer set forth in Example 1. The top coating was made of gelatin only for these five samples.

Sample (8) was prepared by coating a Sixth Layer in a dried thickness of 5.2 microns which contained Emulsified Dispersion F at a coating rate of 1.93 g/m².

Samples (9) to (12) were similarly prepared by replacing Emulsified Dispersion F of Sample (8) by Emulsified Dispersion G for Example (9), by Emulsified Dispersion B for Sample (10), by Emulsified Dispersion C for Sample (11) and by Emulsified Dispersion D for Sample (12), respectively.

The eposure, processing and measurements of optical density all were carried out according to the methods described in Example 1. The results obtained are shown in Table 3 below.

Table 3

| Density Fluctuation* | Sample No. | | | | |
|---|---|---|---|---|---|
| | (8) | (9) | (10) | (11) | (12) |
| Red | 0 | 0 | 0 | 0 | 0 |
| Green | 0 | 0 | 0 | 0 | 0 |
| Blue | 0.14 | 0.13 | 0.06 | 0.06 | 0.05 |

*The values in Table 3 have the same meaning as in Table 2.

The results in Table 3 above show that the compound of the present invention cuts ultraviolet light quite effectively and thus prevents a shift in the color balance due to the difference in the lens properties even when the compound of the present invention is added to the blue sensitive silver halide emulsion layer.

EXAMPLE 3

Samples (1), (2), (3), (4), (5), (6) and (7) produced as described in Example 1 were subjected to the following evaluation for prevention of static marks.

A rubber roller, positioned substantially neutral in the triboelectric series was rolled back and forth on the top, protective coating of each sample film under frictional engagement therewith fifty times in the dark. During this procedure, light was generated due to electric discharge. Each sample, then, was processed as described in Example 1, and the optical density difference between the most dense part in the static marks and the most transparent, background area was measured. The results obtained are shown in Table 4 below.

Table 4

| Density Difference | Sample No. | | | | | | |
|---|---|---|---|---|---|---|---|
| | (1) | (2) | (3) | (4) | (5) | (6) | (7) |
| Red | 0 | 0 | 0 | 0 | 0 | 0 | 0 |
| Green | 0 | 0 | 0 | 0 | 0 | 0 | 0 |
| Blue | 1.05 | 0.25 | 0.15 | 0.15 | 0.15 | 0.80 | 0.65 |

The red, green and blue densities listed in Table 4 above are the densities obtained using red, green and blue light. The results in Table 4 above show that the generation of static marks is suppressed by the use of the compounds of the present invention.

EXAMPLE 4

Emulsified Dispersion H was prepared by first dissolving 10 g of Compound 1 into 5 ml of tricresyl phosphate and 10 ml of ethyl acetate, and then dispersing the resultant solution into 100 g of a 10% aqueous gelatin solution containing sodium dodecyl benzene sulfonate.

This Emulsified Dispersion H was blended with 80 g of a 10% aqueous gelatin solution, to which a gelatin hardening agent and a coating aid had been added. This mixture was coated as the Fourth Layer of a multi-layered sample (Sample (13)) which is described in Table 5 below.

A comparative sample (Sample (14)) was prepared in exactly the same manner as described above for Sample (13) except that another emulsified dispersion than Emulsified Dispersion H was employed in the Fourth Layer. The coating mixture for the Fourth Layer was prepared by first dispersing 10 g of 2-(2-hydroxy-5-tert-butyl)phenyl-benzotriazole in place of Compound 1 in the same manner as above, and blending the resultant dispersion into 20 g of a 10% aqueous gelatin solution with further additions of a gelatin hardening agent and a coating aid.

The coating amounts of the ultraviolet absorbing agent, gelatin and tricresyl phosphate present in the Fourth Layer are shown in the following table (Table 6). Sample (15) did not contain any ultraviolet light absorbing agent and is a comparison sample along with Sample (14).

Table 5

| Layer No. | Composition |
|---|---|
| Sixth | Gelatin (coating amount (C.A.); 1000 mg/m$^2$) |
| Fifth | Red sensitive silver chlorobromide emulsion (Br-50 mole %, C.A.; 300 mg/m$^2$ Ag) containing cyan coupler*$^1$ (C.A.; 400 mg/m$^2$), gelatin (C.A.; 1000 mg/m$^2$) and coupler solvent*$^2$ (C.A.; 200 mg/m$^2$). |

Table 5-continued

| Layer No. | Composition |
|---|---|
| Fourth | Gelatin (C.A.; 1200 mg/m$^2$) containing UV absorber-containing-dispersion as described in Table 6 below |
| Third | Green sensitive silver chlorobromide emulsion (Br-50 mole %, C.A.; 400 mg/m$^2$ Ag), containing magenta coupler*$^3$ (C.A.; 300 mg/m$^2$), gelatin (C.A.; 1000 mg/m$^2$), coupler solvent*$^4$ (C.A.; 300 mg/m$^2$) and dioctylhydroquinone (C.A.; 60 mg/m$^2$). |
| Second | Gelatin (C.A.; 1000 mg/m$^2$) |
| First | Blue sensitive silver chlorobromide emulsion (Br-80 mole %, C.A.; 400 mg/m$^2$ Ag) containing yellow coupler*$^5$ (C.A.; 300 mg/m$^2$) gelatin (C.A.; 1200 mg/m$^2$) and coupler solvent*$^2$ (C.A.; 150 mg/m$^2$) |
| Substrate | |

*$^1$2-[α-(2,4-Di-t-aminophenoxy)butanamido]-4,6-dichloro-5-methylphenol
*$^2$Dibutyl phthalate
*$^3$1-(2,4,6-Trichlorophenyl)-3-[(2-chloro-5-tetradecan-amido)anilino]-5-pyrazolone
*$^4$Tricresyl phosphate
*$^5$α-Pivaloyl-α-(2,4-dioxo-5,5-dimethyloxazolidin-3-yl)-2-chloro-5-[α-(2,4-di-t-amylphenoxy)butanamido]-acetanilide Table 6

| Components in Emulsified Dispersion containing UV Absorbing Agent | Coating Rate in Fourth Layer (mg/m$^2$) | | |
|---|---|---|---|
| | Sample (13) | Sample (14) | Sample (15) |
| Compound 1 | 400 | 0 | 0 |
| 2-(2-Hydroxy-5-t-butyl)-phenyl benzotriazole | 0 | 1000 | 0 |
| Tricresyl Phosphate | 200 | 500 | 0 |
| Gelatin | 1200 | 1200 | 1200 |

Each of these samples was exposed for one second to an optical wedge in which the density changed continuously through a green filter at a light intensity of 1000 lux. The exposed sample was then processed under the following processing condistions with the following processing solutions.

Processing Conditions:
Color Development: 33° C., 3 min 30 sec.
Blix: 33° C., 1 min 30 sec.
Water Washing: 28° C.–35° C., 3 min.
Color Developing Solution:
Benzyl Alcohol: 15 ml
Na$_2$SO$_3$: 5 g
KBr: 0.4 g
Hydroxylamine Sulfate: 2.0 g
4-Amino-3-methyl-N-ethyl-N-β-(methanesulfonamido)ethylaniline: 10.0 g
Na$_2$CO$_3$: 30.0 g
Diethylene Triamine Pentaacetate: 5.0 g
Water to make: 1000 ml
pH = 10.1
Blix Solution:
Ammonium Thiosulfate (70 wt.% aq. soln.) 150 ml
Na$_2$SO$_3$: 5 g
EDTA-Fe(III) Sodium Salt: 40 g
EDTA: 4 g
Water to make: 1000 ml
pH = 6.8

The samples in which magenta dye images had been thus formed were evaluated as to image fading using a fade-meter (20,000 luxes) with a fluorescent lamp for 2 weeks. The results obtained are shown in Table 7 below.

Table 7

| Sample No. | Density Change Before and After Fading Test | |
|---|---|---|
| | Staining at Unexposed Area | Fading at Initial Density of 2.0 |
| (13)* | +0.04 | −0.60 |
| (14)** | +0.05 | −0.65 |
| (15)** | +0.30 | −0.80 |

*Present Invention
**Comparison sample

In Table 7, the stain increase was measured by the yellow density at the undeveloped areas using blue light. The degree of fading was obtained by measuring the density change to green light at the area where the green density was 2.0 prior to the fading test.

Although the coating amount of the UV absorbing agent in Sample (13) of the present invention is only 40% of that of the comparison UV absorbing agent in Sample (14), a better result was achieved.

EXAMPLE 5

Into 5 ml of tricresyl phosphate, 10 g of a cyan coupler, 2-[α-(2,4-di-t-amylphenoxy)butanamido]-4,6-dichloro-5-methylphenol and 2 g of Compound 12 of the present invention were dissolved. The resultant solution was emulsified into 80 g of a 10% gelatin solution containing sodium dodecylbenzene sulfonate. Sample (16) was prepared by blending this dispersion into 145 g of a red sensitive silver chlorobromide emulsion (Br: 50 mole%; Ag content: 7.5 g) together with a gelatin hardener and a coating aid, and then coating the thus-prepared coating mixture on a substrate comprising a paper base laminated on both surfaces with a polyethylene film.

The same procedures were exactly repeated to prepare Sample (17) except that 6 g of 2-(2-hydroxy-5-tert-butyl)phenolbenzotriazole was used as a UV absorber in place of Compound 12, and also to prepare Sample (18) except that no UV absorbing agent was added to the emulsified dispersion containing the cyan coupler.

Each of these three samples was exposed for one second to a continuous optical wedge through a red filter at a light intensity of 1000 lux and then processed in the same manner as in Example 1. The processed samples were subjected to fading testing using a xenon fade meter at a light intensity of 200,000 lux for 2 days.

Table 8 shows the degree of fading of the cyan dye image which had an initial density of 2.0 prior to the fading testing.

Table 8

| Sample No. | Density Change |
|---|---|
| (16)* | −0.30 |
| (17)** | −0.30 |
| (18)** | −0.50 |

*Present invention
**Comparison sample

It is evident from the results in Table 8 that Sample (16) prepared in accordance with the present invention was substantially equivalent to Sample (17) with respect to the light fastness of the cyan image although Sample (16) contained only one third as much a quantity of a UV absorbing agent as Sample (17).

While the invention has been described in detail and with reference to specific embodiments thereof, it will be apparent to one skilled in the art that various changes and modifications can be made therein without departing from the spirit and scope thereof.

What is claimed is:

1. A silver halide photographic material comprising a support having thereon at least one photographic silver halide emulsion layer, with the silver halide photographic material containing, as an ultraviolet light absorbing agent, at least one compound represented by the general formula (I)

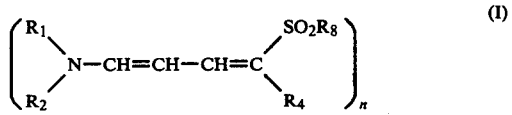

wherein $R_1$ and $R_2$, which may be the same or different, each represents an alkyl group having 1 to 20 carbon atoms; $R_4$ represents $-COOR_6$ or $-COR_6$, wherein $R_6$ represents an alkyl group having 1 to 20 carbon atoms or an aryl group having 6 to 20 carbon atoms and $R_8$ represents an aryl group having 6 to 20 carbon atoms; and n represents an integer of 1 or 2, and when n is 2, at least one of $R_1$, $R_2$ and $R_6$ represents an alkylene group or an arylene group and the compound of the general formula (I) is a dimer.

2. The silver halide photographic material of claim 1, wherein at least one compound represented by the general formula (I) is present in said photographic material in the form of an emulsified dispersion or in the form of a latex dispersion.

3. The silver halide photographic material of claim 1, wherein said silver halide photographic material contains at least one light-insensitive layer and wherein at least one compound represented by the general formula (I) is present in said light-insensitive layer of said photographic material.

4. The silver halide photographic material of claims 1, 2 or 3, wherein said compound represented by the general formula (I) is

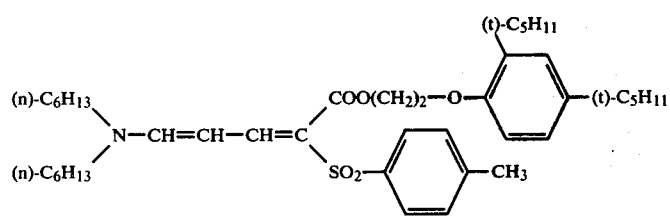

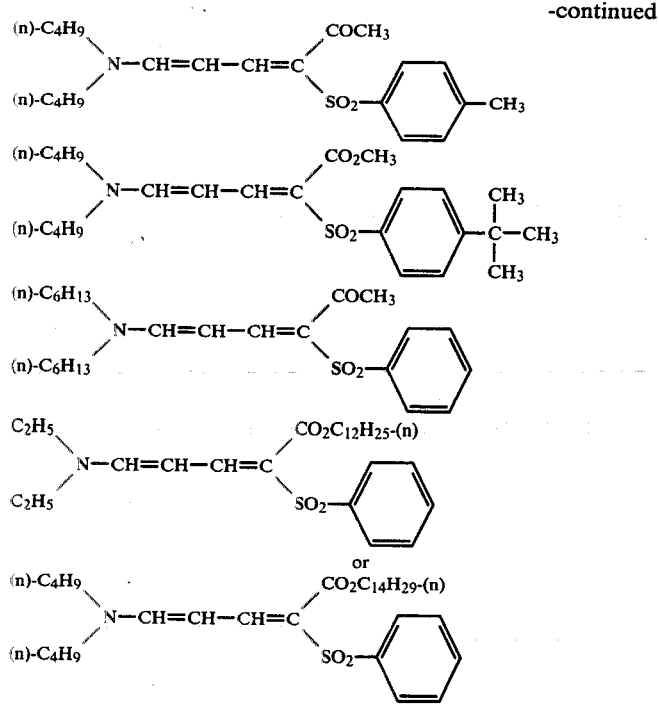

5. The silver halide photographic material of claims 1, 2 or 3, wherein said silver halide photographic material is a multi-layer color photographic material comprising a support having thereon at least one red sensitive silver halide emulsion layer, at least one green sensitive silver halide emulsion layer, at least one blue sensitive silver halide emulsion layer and at least one light insensitive layer.

6. The silver halide photographic material of claim 5, wherein said silver halide photographic material comprises a support having thereon, in order from the support, an antihalation layer, a red sensitive silver halide emulsion layer containing a cyan dye-forming coupler, an interlayer, a green sensitive silver halide emulsion layer containing a magenta dye-forming coupler, a yellow filter layer, a blue sensitive silver halide emulsion layer containing a yellow dye-forming coupler and a protective layer.

7. The silver halide photographic material of claim 2, wherein said latex dispersion comprises at least one of a polymer containing one or more of an alkyl acrylate, an alkyl methacrylate, an alkoxyalkyl acrylate, an alkoxyalkylmethacrylate, a glycidyl acrylate, a glycidyl methacrylate, acrylamide, methacrylamide, a vinyl ester, acrylonitrile, an olefin, and styrene, as a monomer, and a polymer containing one or more of the above monomers and one or more of acrylic acid, methacrylic acid, an α,β-unsaturated dicarboxylic acid, a hydroxyalkyl acrylate, a hydroxyalkyl methacrylate, a sulfoalkyl acrylate, a sulfoalkyl methacrylate, and styrenesulfonic acid, as a monomer.

8. The silver halide photographic material of claim 6, wherein at least one compound represented by the general formula (I) is present in at least one of said protective layer and said blue sensitive silver halide emulsion layer.

9. The silver halide photographic material of claim 1, wherein said silver halide photographic material additionally contains at least one light insensitive layer.

10. A method of preventing the effects of ultraviolet light on a silver halide photographic material comprising a support having thereon at least one silver halide photographic emulsion layer comprising incorporating, as an ultraviolet absorbing agent, at least one compound represented by the following general formula (I)

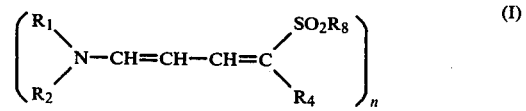

wherein $R_1$ and $R_2$, which may be the same or different, each represents an alkyl group having 1 to 20 carbon atoms; $R_4$ represents —$COOR_6$ or —$COR_6$, wherein $R_6$ represents an alkyl group having 1 to 20 carbon atoms or an aryl group having 6 to 20 carbon atoms and $R_8$ represents an aryl group having 6 to 20 carbon atoms; and n represents an integer of 1 or 2, and when n is 2, at least one of $R_1$, $R_2$ and $R_6$ represents an alkylene group or an arylene group and the compound of the general formula (I) is a dimer.

11. The method of claim 10, wherein at least one compound represented by the general formula (I) is present in said photographic material in the form of an emulsified dispersion or of a latex dispersion.

12. The method of claim 10, wherein the silver halide photographic material contains at least one light-insensitive layer and said at least one compound represented by the general formula (I) is present in said light-insensitive layer of said photographic material.

13. The method of claim 10, wherein said compound represented by the general formula (I) is an oil at room temperature or a solid having a melting point of about 130° C. or lower.

14. The method of claims 10, 11 or 12, wherein said compound represented by the general formula (I) is

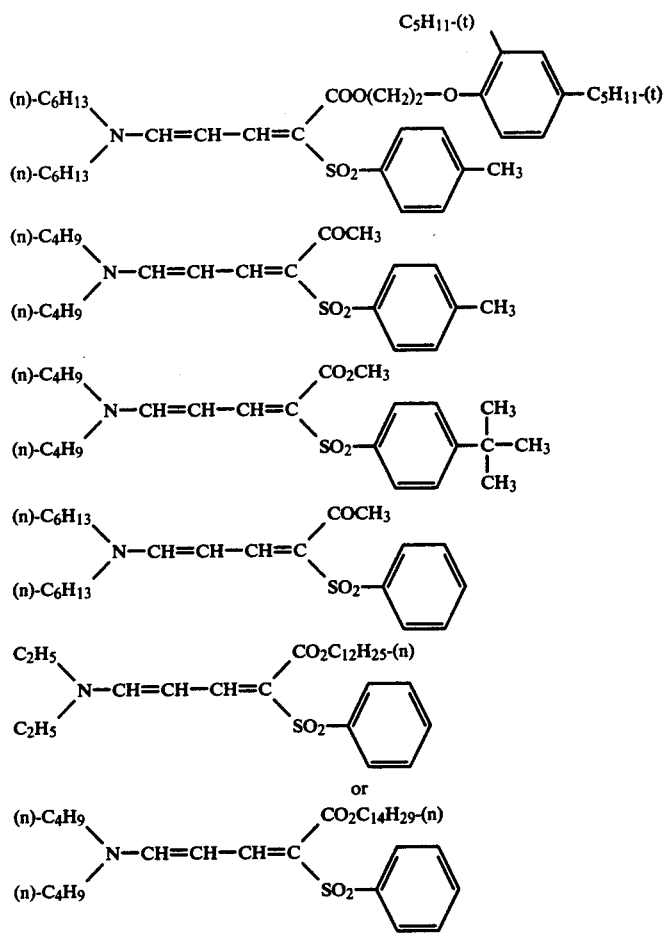

15. The method of claims 10, 11 or 12, wherein said silver halide photographic material is a multi-layered color photographic material comprising a support having thereon at least one red sensitive silver halide emulsion layer, at least one green sensitive silver halide emulsion layer, at least one blue sensitive silver halide emulsion layer and at least one light-insensitive layer.

16. The method of claim 15, wherein said silver halide photographic material comprises a support having thereon, in order from the support, an antihalation layer, a red sensitive silver halide emulsion layer containing a cyan dye-forming coupler, an interlayer, a green sensitive silver halide emulsion layer containing a magenta dye-forming coupler, a yellow filter layer, a blue sensitive silver halide emulsion layer containing a yellow dye-forming coupler and a protective layer.

17. The method of claim 11, wherein said latex dispersion comprises at least one of a polymer containing one or more of an alkyl acrylate, an alkyl methacrylate, an alkoxyalkyl acrylate, an alkoxyalkyl methacrylate, a glycidyl acrylate, glycidyl methacrylate, acrylamide, methacrylamide, a vinyl ester, acryonitrile, an olefin, and styrene, as a monomer, and a polymer of combinations of the above monomers and one or more of acrylic acid, methacrylic acid, an α,β-unsaturated dicarboxylic acid, a hydroxyalkyl acrylate, a hydroxyalkyl methacrylate, a sulfoalkyl acrylate, a sulfoalkyl methacrylate, and styrenesulfonic acid, as a monomer.

18. The method of claim 16, wherein at least one compound represented by the general formula (I) is present in at least one of said protective layer and said blue sensitive silver halide emulsion layer.

19. The method of claims 10, 11 or 12, wherein at least one compound represented by the general formula (I) is present in said silver halide photographic material at a coating amount of from about 5 to about 1500 mg/m² of said photographic material.

20. The silver halide photographic material of claim 1, wherein said ultraviolet light absorbing agent is

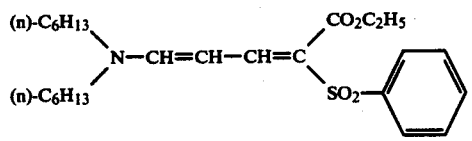

21. The silver halide photographic material of claim 1, wherein said ultraviolet light absorbing agent is

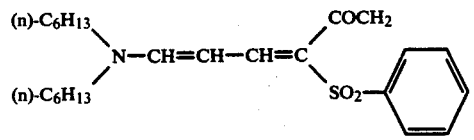

22. The silver halide photographic material of claim 1, wherein said ultraviolet light absorbing agent is

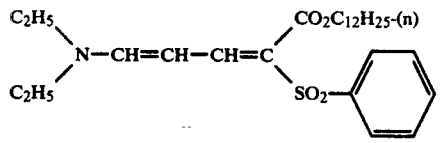
23. The method of claim 10, wherein said ultraviolet absorbing agent is
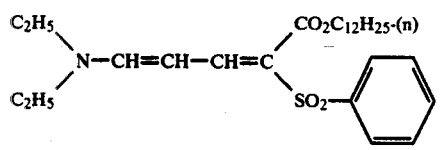
24. The method of claim 10, wherein said ultraviolet absorbing agent is
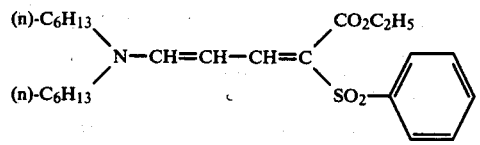
25. The method of claim 10, wherein said ultraviolet absorbing agent is
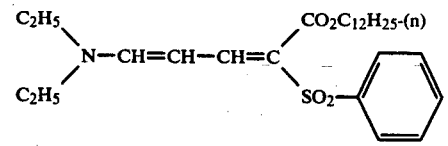
* * * * *